US011856974B2

(12) United States Patent
Markosyan

(10) Patent No.: US 11,856,974 B2
(45) **Date of Patent: *Jan. 2, 2024**

(54) HIGHLY SOLUBLE STEVIA SWEETENER

(71) Applicant: PureCircle Sdn Bhd, Kuala Lumpur (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 218 days.

This patent is subject to a terminal disclaimer.

(21) Appl. No.: 15/250,550

(22) Filed: Aug. 29, 2016

(65) Prior Publication Data

US 2016/0360775 A1 Dec. 15, 2016

Related U.S. Application Data

(63) Continuation of application No. 13/984,315, filed as application No. PCT/US2012/024585 on Feb. 10, 2012, now Pat. No. 9,427,006.

(60) Provisional application No. 61/441,443, filed on Feb. 10, 2011.

(51) Int. Cl.

| | |
|---|---|
| ***A23L 27/30*** | (2016.01) |
| ***A23L 27/10*** | (2016.01) |
| ***A23L 27/00*** | (2016.01) |
| ***A23L 27/12*** | (2016.01) |
| ***A23L 33/21*** | (2016.01) |
| ***A23G 3/36*** | (2006.01) |
| ***A23G 9/32*** | (2006.01) |
| ***A23L 2/60*** | (2006.01) |
| ***A61K 8/60*** | (2006.01) |
| ***A61Q 19/00*** | (2006.01) |
| ***A61K 36/28*** | (2006.01) |
| ***A61K 8/9789*** | (2017.01) |
| *A23L 27/21* | (2016.01) |

(52) U.S. Cl.

CPC ................ *A23L 27/33* (2016.08); *A23G 3/36* (2013.01); *A23G 9/32* (2013.01); *A23L 2/60* (2013.01); *A23L 27/00* (2016.08); *A23L 27/10* (2016.08); *A23L 27/11* (2016.08); *A23L 27/12* (2016.08); *A23L 27/30* (2016.08); *A23L 27/31* (2016.08); *A23L 27/34* (2016.08); *A23L 27/35* (2016.08); *A23L 27/36* (2016.08); *A23L 27/37* (2016.08); *A23L 33/21* (2016.08); *A61K 8/602* (2013.01); *A61K 8/9789* (2017.08); *A61K 36/28* (2013.01); *A61Q 19/00* (2013.01); *A23L 27/21* (2016.08); *A23V 2002/00* (2013.01); *A61K 2800/10* (2013.01); *A61K 2800/92* (2013.01)

(58) Field of Classification Search

CPC .......... A23L 27/33; A23L 27/11; A23L 27/30; A23L 2/60

See application file for complete search history.

(56) References Cited

U.S. PATENT DOCUMENTS

| | | | |
|---|---|---|---|
| 3,723,410 | A | 3/1973 | Persinos |
| 4,082,858 | A | 4/1978 | Morita et al. |
| 4,171,430 | A | 10/1979 | Matsushita et al. |
| 4,219,571 | A | 8/1980 | Miyake |
| 4,361,697 | A | 11/1982 | Dobberstein et al. |
| 4,454,290 | A | 6/1984 | Dubois |
| 4,590,160 | A | 5/1986 | Nishihashi et al. |
| 4,599,403 | A | 7/1986 | Kumar |
| 4,612,942 | A | 9/1986 | Dobberstein et al. |
| 4,657,638 | A | 4/1987 | le Grand et al. |
| 4,892,938 | A | 1/1990 | Giovanetto |
| 4,917,916 | A | 4/1990 | Hirao et al. |
| 5,112,610 | A | 5/1992 | Kienle |
| 5,576,042 | A | 11/1996 | Fuisz |
| 5,779,805 | A | 7/1998 | Morano |
| 5,962,678 | A | 10/1999 | Payzant et al. |
| 5,972,120 | A | 10/1999 | Kutowy et al. |
| 6,031,157 | A | 2/2000 | Morita et al. |
| 6,080,561 | A | 6/2000 | Morita et al. |
| 6,204,377 | B1 | 3/2001 | Nishimoto et al. |
| 6,228,996 | B1 | 5/2001 | Zhou et al. |
| 6,706,304 | B1 | 3/2004 | Ishida et al. |
| 7,807,206 | B2 | 10/2010 | Magomet et al. |
| 7,838,044 | B2 | 11/2010 | Abelyan et al. |
| 7,862,845 | B2 | 1/2011 | Magomet et al. |
| 8,257,948 | B1 | 9/2012 | Markosyan |
| 2002/0132320 | A1 | 9/2002 | Wang et al. |
| 2003/0161876 | A1 | 8/2003 | Hansson et al. |
| 2003/0232118 | A1 | 12/2003 | Erchenfeld et al. |
| 2003/0236399 | A1 | 12/2003 | Zheng et al. |
| 2006/0083838 | A1 | 4/2006 | Jackson |
| 2006/0134292 | A1 | 6/2006 | Abelyan et al. |

(Continued)

FOREIGN PATENT DOCUMENTS

| | | |
|---|---|---|
| BR | 210701736 | 7/2008 |
| CN | 1049666 | 3/1991 |

(Continued)

OTHER PUBLICATIONS

JECFA "Steviol Glycosides" FAO JECFA Monographs 5 (2008) pp. 1-4.*

(Continued)

*Primary Examiner* — Jyoti Chawla

(74) *Attorney, Agent, or Firm* — Rachael Casey

(57) ABSTRACT

A method for making a highly soluble Stevia sweetener is described. The resulting sweetener readily provides solutions with up to or greater than 30% concentration which are stable for more than 24 hours.

1 Claim, No Drawings

(56) References Cited

U.S. PATENT DOCUMENTS

| | | | | |
|---|---|---|---|---|
| 2006/0142555 | A1 | 6/2006 | Jonnala et al. | |
| 2007/0082102 | A1 | 4/2007 | Magomet et al. | |
| 2007/0082103 | A1 | 4/2007 | Magomet et al. | |
| 2007/0116800 | A1 | 5/2007 | Prakash | |
| 2007/0116819 | A1 | 5/2007 | Prakash | |
| 2007/0116820 | A1 | 5/2007 | Prakash | |
| 2007/0116821 | A1 | 5/2007 | Prakash | |
| 2007/0116822 | A1 | 5/2007 | Prakash | |
| 2007/0116823 | A1 | 5/2007 | Prakash | |
| 2007/0116824 | A1 | 5/2007 | Prakash | |
| 2007/0116825 | A1 | 5/2007 | Prakash | |
| 2007/0116826 | A1 | 5/2007 | Prakash | |
| 2007/0116827 | A1 | 5/2007 | Prakash | |
| 2007/0116828 | A1 | 5/2007 | Prakash | |
| 2007/0116829 | A1 | 5/2007 | Prakash | |
| 2007/0116830 | A1 | 5/2007 | Prakash | |
| 2007/0116831 | A1 | 5/2007 | Prakash | |
| 2007/0116832 | A1 | 5/2007 | Prakash | |
| 2007/0116833 | A1 | 5/2007 | Prakash | |
| 2007/0116834 | A1 | 5/2007 | Prakash | |
| 2007/0116835 | A1 | 5/2007 | Prakash | |
| 2007/0116836 | A1 | 5/2007 | Prakash | |
| 2007/0116837 | A1 | 5/2007 | Prakash | |
| 2007/0116838 | A1 | 5/2007 | Prakash | |
| 2007/0116839 | A1 | 5/2007 | Prakash | |
| 2007/0116840 | A1 | 5/2007 | Prakash | |
| 2007/0116841 | A1 | 5/2007 | Prakash | |
| 2007/0128311 | A1 | 6/2007 | Prakash | |
| 2007/0134390 | A1 | 6/2007 | Prakash | |
| 2007/0134391 | A1 | 6/2007 | Prakash | |
| 2007/0224321 | A1 | 9/2007 | Prakash | |
| 2007/0292582 | A1* | 12/2007 | Prakash | C07H 1/08 426/548 |
| 2008/0064063 | A1 | 3/2008 | Brandle et al. | |
| 2008/0102497 | A1 | 5/2008 | Wong et al. | |
| 2008/0107775 | A1 | 5/2008 | Prakash | |
| 2008/0107776 | A1 | 5/2008 | Prakash | |
| 2008/0107787 | A1 | 5/2008 | Prakash | |
| 2008/0108710 | A1 | 5/2008 | Prakash | |
| 2008/0111269 | A1 | 5/2008 | Politi et al. | |
| 2008/0226797 | A1 | 9/2008 | Lee et al. | |
| 2008/0292764 | A1 | 11/2008 | Prakash | |
| 2008/0292765 | A1 | 11/2008 | Prakash | |
| 2008/0292775 | A1 | 11/2008 | Prakash et al. | |
| 2008/0300402 | A1 | 12/2008 | Yang et al. | |
| 2009/0017185 | A1 | 1/2009 | Catani | |
| 2009/0053378 | A1 | 2/2009 | Prakash | |
| 2009/0074935 | A1 | 3/2009 | Lee | |
| 2009/0079935 | A1 | 3/2009 | Harris et al. | |
| 2009/0142817 | A1 | 6/2009 | Norman et al. | |
| 2009/0226590 | A1 | 9/2009 | Fouache et al. | |
| 2010/0055752 | A1 | 3/2010 | Kumar | |
| 2010/0056472 | A1 | 3/2010 | Duan et al. | |
| 2010/0057024 | A1 | 3/2010 | Bernard | |
| 2010/0099857 | A1 | 4/2010 | Evans | |
| 2010/0112159 | A1 | 5/2010 | Abelyan et al. | |
| 2010/0120710 | A1 | 5/2010 | Watanabe et al. | |
| 2010/0137569 | A1 | 6/2010 | Prakash et al. | |
| 2010/0189861 | A1 | 7/2010 | Abelyan et al. | |
| 2010/0227034 | A1 | 9/2010 | Purkayastha et al. | |
| 2010/0255171 | A1 | 10/2010 | Purkayastha et al. | |
| 2010/0278993 | A1 | 11/2010 | Prakash et al. | |
| 2010/0316782 | A1 | 12/2010 | Shi et al. | |
| 2011/0030457 | A1 | 2/2011 | Valery et al. | |
| 2011/0033525 | A1 | 2/2011 | Liu | |
| 2011/0092684 | A1 | 4/2011 | Abelyan et al. | |
| 2011/0104353 | A1 | 5/2011 | Lee | |
| 2011/0111115 | A1 | 5/2011 | Shi et al. | |
| 2011/0124587 | A1 | 5/2011 | Jackson et al. | |
| 2011/0160311 | A1 | 6/2011 | Prakash et al. | |
| 2011/0189360 | A1* | 8/2011 | Yoo | A23L 2/60 426/330.3 |
| 2011/0195169 | A1 | 8/2011 | Markosyan et al. | |
| 2012/0164678 | A1 | 6/2012 | Stephanopoulos et al. | |
| 2012/0214752 | A1 | 8/2012 | Markosyan | |

FOREIGN PATENT DOCUMENTS

| | | | |
|---|---|---|---|
| CN | 1100727 | 3/1995 | |
| CN | 1112565 | 11/1995 | |
| CN | 1192447 | 9/1998 | |
| CN | 1238341 | 12/1999 | |
| CN | 1349997 | 5/2002 | |
| CN | 101200480 | 6/2008 | |
| CN | 101591365 | 12/2011 | |
| EP | 2486806 | 8/2012 | |
| JP | 52005800 | 1/1977 | |
| JP | 52083731 | 7/1977 | |
| JP | 52100500 | 8/1977 | |
| JP | 52136200 | 11/1977 | |
| JP | 54030199 | 3/1979 | |
| JP | 54132599 | 10/1979 | |
| JP | 55039731 | 3/1980 | |
| JP | 55081567 | 6/1980 | |
| JP | 55092400 | 7/1980 | |
| JP | 65120770 | 9/1980 | |
| JP | 65138372 | 10/1980 | |
| JP | 55162953 | 12/1980 | |
| JP | 65159770 | 12/1980 | |
| JP | 56099768 | 8/1981 | |
| JP | 56109568 | 8/1981 | |
| JP | 56121453 | 9/1981 | |
| JP | 56121454 | 9/1981 | |
| JP | 56121455 | 9/1981 | |
| JP | 56160962 | 12/1981 | |
| JP | 57002656 | 1/1982 | |
| JP | 57005663 | 1/1982 | |
| JP | 57046998 | 3/1982 | |
| JP | 57075992 | 5/1982 | |
| JP | 57086264 | 5/1982 | |
| JP | 58020170 | 2/1983 | |
| JP | 58028246 | 2/1983 | |
| JP | 58028247 | 2/1983 | |
| JP | 58212759 | 12/1983 | |
| JP | 58212760 | 12/1983 | |
| JP | 59045848 | 3/1984 | |
| JP | 62166861 | 7/1987 | |
| JP | 63173531 | 7/1988 | |
| JP | H0195739 | 4/1989 | |
| JP | 1131191 | 5/1989 | |
| JP | 3262458 | 11/1991 | |
| JP | 6007108 | 1/1994 | |
| JP | 6192283 | 7/1994 | |
| JP | 7143860 | 6/1995 | |
| JP | 7177862 | 7/1995 | |
| JP | 8000214 | 1/1996 | |
| JP | 9107913 | 4/1997 | |
| JP | 2000236842 | 9/2000 | |
| JP | 2002262822 | 9/2002 | |
| JP | 2004344071 | 12/2004 | |
| JP | 2010516764 | 5/2010 | |
| KR | 20070067199 | 6/2007 | |
| KR | 20080071605 | 8/2008 | |
| KR | 20090021386 | 3/2009 | |
| RU | 2111969 | 5/1998 | |
| RU | 2123267 | 12/1998 | |
| RU | 2156083 | 9/2000 | |
| RU | 2167544 | 5/2001 | |
| RU | 2198548 | 2/2003 | |
| WO | 2005089483 | 9/2005 | |
| WO | 2006072878 | 7/2006 | |
| WO | 2006072879 | 7/2006 | |
| WO | 2008091547 | 7/2008 | |
| WO | WO-2008112957 A1 * | 9/2008 | A23C 11/103 |
| WO | 2009108680 | 9/2009 | |
| WO | 2010118218 | 10/2010 | |
| WO | 2011059954 | 5/2011 | |
| WO | 2011153378 | 12/2011 | |
| WO | 2012082493 | 6/2012 | |
| WO | 2012082677 | 6/2012 | |
| WO | 2013022989 | 2/2013 | |
| WO | 2013036366 | 3/2013 | |

OTHER PUBLICATIONS

(56) References Cited

OTHER PUBLICATIONS

Emperor's Herbologist "Stevioside Comparison" pp. 1-5 Jan. 22, 2010 http://emperorsherbologist.com/steviacompare.php (Year: 2010).*
A-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3, 1999 , 277-282.
Chen, et al., "Selectivity of polymer adsorbent in adsorptive separations of stevia diterpene glycisides", Science in China, vol. 41, No. 4, 1998 , 436-441.
Chen, et al., "Studies on the adsorptive selectivity of the polar resin with carbonyl group on rebaudioside A", Acta Polymeric Scnica, No. 4, 1999 , 398-403.
Crammer, et al., "Sweet glycosides from the Stevia plant", Chemistry in Britain, Oct. 1986, 915-916, 918.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
Fuh, "Purification of steviosides by membrane and ion exchange process", Journal of Food Science, vol. 55, No. 5, 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography, vol. 464 (1989) 213-219.
Hale, et al., "Amylase of Bacillus Macerans", Cereal Chemistry, vol. 28, No. 1, Jan. 1951, 49-58.
Hartel, Richard "Crystallization in Foods" Handbook of Industrial Crystallization Elsevier 2002, pp. 287 and 293-296.
International Search Report and Written Opinion of PCT/US20101055960, pp. 1-11, dated Jan. 2011.
International Search Report and Written Opinion of PCT/US2011/036063, dated Aug. 5, 2011, pp. 1-7.
International Search Report and Written Opinion of PCT/US2011/047498, dated Dec. 22, 2011, pp. 1-8.
International Search Report and Written Opinion of PCT/US2011/047499, dated Dec. 22, 2011, pp. 1-8.
International Search Report and Written Opinion of PCT/US2011/064343, pp. 1-17, dated Jan. 2, 2013.
International Search Report and Written Opinion of PCT/US20111028028, pp. 1-8, dated May 2011.
International Search Report and Written Opinion of PCT/US20111033734, pp. 1-8, dated Jul. 2011.
International Search Report and Written Opinion of PCT/US20111033737, pp. 1-8, dated Jul. 2011.
International Search Report and Written Opinion of PCT/US20111033912, pp. 1-6, dated Jul. 2011.
International Search Report and Written Opinion of PCT/US20111035173, pp. 1-7, dated Aug. 2011
International Search Report and Written Opinion of PCT/US2012/024585, pp. 1-8, dated Jun. 2012.
International Search Report and Written Opinion of PCT/US2012/024722, pp. 1-8, dated May 2012.
International Search Report and Written Opinion of PCT/US2012/030210, pp. 1-10, dated Jul. 2012.
International Search Report and Written Opinion of PCT/US2012/043294, pp. 1-7 , dated Sep. 2012.
International Search Report and Written Opinion of PCT/US2012/051163, pp. 1-9, dated Oct. 2012.
International Search Report and Written Opinion of PCT/US2012/052659, pp. 1-9, dated Nov. 2012.
International Search Report and Written Opinion of PCT/US2012/052665, pp. 1-3, dated Nov. 2012.
International Search Report and Written Opinion of PCT/US20131030439 pp. 1-10, dated May 2013.
Jaitak, et al., "An Efficient Microwave-assisted Extraction Process of Stevioside and Rebaudioside-A from Stevia Rebaudiana (Bertoni)", Phytochem. Anal. vol. 20, 2009 , 240-245.
Kennelly, "Sweet and non-sweet constituents of Stevia rebaudiana", Stevia: The genus *Stevia*, Taylor & Francis, 2002, 68-85.
Kinghorn, "Overview", Stevia: The genus *Stevia*, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989 , 2923-2928.
Kobayashi, et al., "Dulcoside A and B, New diterpene glycosides from Stevia Rebaudiana", Phytochemistry, vol. 16, 1977 , 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15, 1976 , 981-983.
Kovylyaeva, et al., "Glycosides from Stevia rebaudiana", Chemistry of Natural Compounds, vol. 43, No. 1, 2007 , 81-85.
Liu, et al., "Study of stevioside preparation by membrane separation process", Desalination, vol. 83, 1991 , 375-382.
Lobov, S. V. et al., "Enzymic Production of Sweet Stevioside Derivatives: Transglucosylation of Glucosidases", Agric. Biol. Chem., vol. 55, No. 12, 1991 , 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3, 2004, 449-458.
Moraes, et al., "Clarification of Stevia rebaudiana (Bert.) Bertoni extract adsorption in modified zeolites", Acta Scientiarum, vol. 23, No. 6, 2001 , 1375-1380.
Ohta et al., "Characterization of Novel Steviol Glycosides from Leaves of Stevia rebaudiana Morita," J. Appl. Glycosi., vol. 57, 199-209, 2010.
Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.
Phillips, K. C. , "Stevia: steps in developing a new sweetener", In T.H. Grenby, Editor, Developments in Sweeteners-3, Elsevier 1987 , 1-43.
Pol, et al., "Comparison of two different solvents employed for pressurised fluid extraction of stevioside from Stevia rebaudiana: methanol versus water", Anal Bioanal Chem vol. 388 2007 , 1847-1857.
Prakash et al., "Development of rebiana, a natural, non-caloric sweetener," Jul. 1, 2008, Food and Chemical Toxology, vol. 46, Is. 7, Sup. 1, p. S75-S82.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C Nmr Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.
Shi, et al., "Synthesis of bifunctional polymeric adsorbent and its application in purification of Stevia glycosides", Reactive & Functional Polymers, vol. 50, 2002, 107-116.
Shibata et al., "Glucosylation of Steviol and Steviol-Glucosides in Extracts from Stevia rebaudiana Bertoni," Plant Physiol. vol. 95, (1991) 152-156.
Starratt, et al., "Rebaudioside F, a diterpene glycoside from Stevia Rebaudiana", Phytochemistry, vol. 59, 2002 , 367-370.

(56) References Cited

OTHER PUBLICATIONS

Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http://www.accessdataida.gov/scriptsficn/gras_notices/grn000282.pdf (obtained from the WEB on May 8, 2012) entire document esp. p. 22, Table 1, pp. 1-97.
Tanaka, O. , "Improvement of taste of natural sweeteners", Pure & Appl. Chem., vol. 69, No. 4, 1997, 675-683.
Teo, et al., "Validation of green-solvent extraction combined with chromatographic chemical fingerprint to evaluate quality of Stevia rebaudiana Bertoni", J. Sep. Sci, vol. 32, 2009, 613-622.
United Nations' Food and Agriculture Organization/Joint Expert Committee on Food Additives (2010) Steviol Glycosides,Compendium of Food Additive Specifications, FAO JECFA Monographs 10, 17-21.
Van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci_ Biotech. Biochem. vol. 58, No. 9, 1994 , 1657-1661.
Yoda, et al., "Supercritical fluid extraction from Stevia rebaudiana Bertoni using CO2 and CO2+ water: extraction kinetics and identification of extracted components", Journal of Food Engineering, vol. 57, 2003 , 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33, 2000 , 617-620.
Hancock B C et al, "What is the true solubility advantage for amorphous pharmaceuticals?", Pharmaceutical Research, Springer New York LLC, US, (Apr. 1, 2000), vol. 17, No. 4, doi:10.1023/A:1007516718048, ISSN 0724-8741, pp. 397-404, XP009086748 [A] 1-11.
Kikuchi K et al, "Readily soluble sweetening agent prepn.—by processing mixt. of stevioside, prods. from Stevia Rebaudiana Bertonis and water in vacuum drying facility to shape in granular form", WPI / Thomson,, (Apr. 13, 1989), vol. 1989, No. 21, XP002714589 [A] 1-11.

* cited by examiner

HIGHLY SOLUBLE STEVIA SWEETENER

RELATED APPLICATIONS

This application is a continuation application of U.S. patent application Ser. No. 13/984,315, filed on Aug. 28, 2013, the contents of which are incorporated by reference herein, which is a U.S. national phase application of International Application No. PCT/US2012/024585, filed Feb. 10, 2012, which claims the benefit of U.S. Provisional Patent Application No. 61/441,443, filed Feb. 10, 2011.

FIELD OF THE INVENTION

The invention relates to a process for the preparation of highly soluble individual or combined sweet glycosides from a *Stevia rebaudiana* Bertoni plant extract, and more particularly for preparation of highly soluble rebaudioside A.

DESCRIPTION OF THE RELATED ART

It is well known that Rebaudioside A exhibits so called polymorphism (Zell et al., 2000). Rebaudioside A amorphous, anhydrous and solvate forms differ significantly from each other in terms of solubility which is one of the main criteria for the commercial viability of a sweetener. In this regard, as shown in Table 1, the hydrate form of Rebaudioside A displays the lowest solubility (Prakash et al., 2008). It was shown that Rebaudioside A may transform from one polymorph form to another at certain conditions (U.S. pat. appl. Ser. No. 11/556,049).

TABLE 1

Properties of Rebaudioside A forms (US Pat. Appl. 11/556,049)

| | Polymorph Forms | | | |
|---|---|---|---|---|
| | Form 1 Hydrate | Form 2 Anhydrous | Form 3 Solvate | Form 4 Amorphous |
| Rate of dissolution in $H_2O$ at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Patent application WO/2010/118218 describes a process of producing highly soluble rebaudioside A by preparing a highly soluble hydrated crystalline form. However the described methodology utilizes low throughput techniques such as evaporative crystallization or hot filtration/centrifugation of slurries which can be hard to accomplish in large industrial scale.

On the other hand it is known (Prakash et al., 2008) that rebaudioside A amorphous forms prepared by spray drying display high solubility as well. However spray drying of rebaudioside A is a very challenging and low throughput task because generally spray drying requires concentrated feed solutions (about 50% solids content). Rebaudioside A concentrated solutions prepared by simple dissolution are very unstable and tend to crystallize very fast. These concentrated solutions (>10%) prepared by common solubilization methods such as heating under normal conditions crystallize shortly after cooling down to room temperature. Thus spray drying of such solutions requires special equipment capable of maintaining the solution at elevated temperature.

On the other hand extended exposure of rebaudioside A to high temperature both in solid form and in aqueous solutions results in hydrolytic decomposition of the material (Prakash et al., 2008).

Therefore a high throughput process of manufacturing highly soluble Rebaudioside A or other steviol glycosides on an industrial scale without needing a sophisticated equipment setup will offer certain advantages compared to other techniques known to art.

SUMMARY OF THE INVENTION

The invention is directed to a method for producing a sweetener comprising the steps of providing a Stevia sweetener powder and solubilizing it in the water under gradient temperature treatment conditions, to produce a highly stable concentrated solution, and spray drying the highly stable concentrated solution to obtain a highly soluble Stevia sweetener powder.

Hereinafter the term “steviol glycoside(s)” will mean Rebaudioside A, Rebaudioside B, Rebaudioside C, Rebaudioside D, Rebaudioside E, Rebaudioside F, Stevioside, Steviolbioside, Dulcoside A, Rubusoside, or other glycoside of steviol and combinations thereof.

Hereinafter, unless specified otherwise, the solubility of material is determined in RO (reverse osmosis) water at room temperature. Where the solubility is expressed as “%” it to be understood as number of grams of material soluble in 100 grams of solvent.

It is to be understood that both the foregoing general description and the following detailed description are exemplary and explanatory and are intended to provide further explanation of the invention as claimed.

DETAILED DESCRIPTION OF THE INVENTION

A process for the preparation of highly soluble Stevia sweetener, particularly Rebaudioside A, is described herein.

Crystalline Rebaudioside A has an inherently very low solubility, ranging from about 1%-2%. As described above, Rebaudioside A exhibits polymorphism, resulting in a variety of forms with very different characteristics and handling properties. The hydrate form has very low solubility (less than 0.2%), and is therefore not commercially viable as a sweetener. The solvate form has a solubility typically greater than 30%, but this form has only of scientific interest and cannot be used for food or beverage applications because the level of residual alcohol (1-3%) makes it unfit for use in foods and beverages. The anhydrous form has a solubility reported in literature of a maximum of up to about 30% solubility. The amorphous form has as solubility generally greater than 30%, but for its preparation, the crystalline form has to be dissolved in the water at very high concentrations (approx. 50%) which is not achievable by common solubilization techniques.

Typical spray drying techniques involve the use of a highly concentrated, and yet stable, starting solution to achieve the highest output possible. As noted above, crystalline Rebaudioside A has a very low solubility, so to create a stable solution (one which will not crystallize at room temperature), the solution has to be very dilute. Spray drying very dilute solutions is not economically efficient as the output of the spray dried powder will be very low. The need exists, therefore, for a process in which a high solubility Rebaudioside A is obtained by a process which does not require significantly diluted Rebaudioside A solution in order for the solution to be stable at room temperature.

In one embodiment of the present invention, an initial material, comprising sweet glycoside(s) of the *Stevia rebaudiana* Bertoni plant extract, which includes Stevioside, Rebaudioside A, Rebaudioside B, Rebaudioside C, Rebaudioside D, Rebaudioside E, Rebaudioside F, Steviolbioside, Dulcoside A, Rubusoside or other glycoside of steviol and combinations thereof, was combined with water at a ratio of about 1:1 (w/w).

The obtained mixture was further subjected to a gradient heat treatment which resulted in high stability and high concentration solution. The gradient of about 1° C. per minute was used in heating the mixture. The mixture was heated to the temperature of about 110-140° C., preferably about 118-125° C. and was held at maximum temperature for about 0-120 min, preferably about 50-70 min.

After the heat treatment the solution was cooled down to room temperature at gradient of about 1° C. per minute. 24-hour incubation of this high stability and high concentration solution did not show any crystallization.

The solution was spray dried by a laboratory spray drier operating at about 175° C. inlet temperature and about 100° C. outlet temperature. A highly soluble amorphous form of rebaudioside A was obtained with greater than about 30% solubility in water at room temperature.

The following examples illustrate preferred embodiments of the invention. It will be understood that the invention is not limited to the materials, proportions, conditions and procedures set forth in the examples, which are only illustrative.

EXAMPLE 1

Preparation of Rebaudioside A Concentrated Solution 100 g of rebaudioside A containing Stevioside 0.2%, Rebaudioside C 0.3%, Rebaudioside F 0.3%, Rebaudioside A 97.7%, Rebaudioside D 1.0%, and Rebaudioside B 0.3%, all percentages being on a percent dry weight basis, and having water solubility of 0.6% was mixed with 100 g of water and boiled on a laboratory heater until complete dissolution. Upon complete dissolution, the solution was cooled to room temperature to make Solution #1.

EXAMPLE 2

Preparation of Rebaudioside A Concentrated Solution 100 g of rebaudioside A containing Stevioside 0.2%, Rebaudioside C 0.3%, Rebaudioside F 0.3%, Rebaudioside A 97.7%, Rebaudioside D 1.0%, Rebaudioside B 0.3%, all percentages being on a percent dry weight basis, and having water solubility of 0.6% was mixed with 100 g of water and incubated in autoclave (AMA 270, Astell Scientific, UK), at 121° C. for 1 hour. Upon completion of incubation period the obtained clear solution was cooled to room temperature to make Solution #2.

EXAMPLE 3

Preparation of Rebaudioside A Concentrated Solution 100 g of rebaudioside A containing Stevioside 0.2%, Rebaudioside C 0.3%, Rebaudioside F 0.3%, Rebaudioside A 97.7%, Rebaudioside D 1.0%, Rebaudioside B 0.3%, all percentages being on a percent dry weight basis, and having water solubility of 0.6% was mixed with 100 g of water and incubated in thermostatted oil bath. The temperature was increased at 1° C. per minute to 121° C. The mixture was maintained at 121° C. for 1 hour and then the temperature was decreased to room temperature (25° C.) at 1° C. per minute to make Solution #3.

EXAMPLE 4

Rebaudioside A Concentrated Solution Stability

Rebaudioside A Solution #1, Solution #2 and Solution #3 prepared according to EXAMPLE 1, EXAMPLE 2 and EXAMPLE 3, respectively, were assessed in terms of their stability at room temperature (25° C.). The results are summarized in Table 2.

TABLE 2

Rebaudioside A concentrated solution stability (50% total solids, 25° C.)

| Time, hrs | Observation Solution #1 | Solution #2 | Solution #3 |
|---|---|---|---|
| 0.5 | Clear solution | Clear solution | Clear solution |
| 1 | Intensive crystallization | Cloudy solution, precipitate on the bottom | Clear solution |
| 2 | Viscous slurry of crystals | Intensive crystallization | Clear solution |
| 4 | Solidified crystalline mixture | Viscous slurry of crystals | Clear solution |
| 24 | Solidified crystalline mixture | Solidified crystalline mixture | Clear solution |

It can be seen that the solution prepared by temperature gradient method shows greater stability against crystallization.

EXAMPLE 5

Preparation of Highly Soluble Rebaudioside A

Rebaudioside A Solution #1, Solution #2 and Solution #3 prepared according to EXAMPLE 1, EXAMPLE 2 and EXAMPLE 3, respectively, were dried using YC-015 laboratory spray drier (Shanghai Pilotech Instrument & Equipment Co. Ltd., China) operating at 175° C. inlet and 100° C. outlet temperature. Solution #1 and Solution #2 had to be maintained at 80° C. to prevent premature crystallization whereas Solution #3 was maintained at room temperature. The Solution #1 yielded Sample #1, Solution #2 yielded Sample #2 and Solution #3 yielded Sample #3.

The obtained amorphous powder samples were compared for solubility (Table 3).

TABLE 3

Highly soluble Rebaudioside A

| Solubility, % | Observation Sample #1 | Sample #2 | Sample #3 |
|---|---|---|---|
| 5 | Clear solution | Clear solution | Clear solution |
| 10 | Slightly cloudy solution | Clear solution | Clear solution |

TABLE 3-continued

| Highly soluble Rebaudioside A | | | |
|---|---|---|---|
| Solubility, | Observation | | |
| % | Sample #1 | Sample #2 | Sample #3 |
| 20 | Cloudy solution | Slightly cloudy solution | Clear solution |
| 30 | Undissolved matter on the bottom | Cloudy solution | Clear solution |
| 40 | Significant amount of undissolved matter | Significant amount of undissolved matter | Slightly cloudy solution |

The process of the present invention resulted in a Rebaudioside A polymorph which demonstrated high degree of solubility in water. Although the foregoing embodiments describe the use of Rebaudioside A, it is to be understood that any Stevia-based sweetener may be used and prepared in accordance with this invention, and all Stevia-based sweeteners are contemplated to be within the scope of the present invention.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

I claim:

1. A Rebaudioside A concentrated solution made by a method comprising the steps of:

A) providing a crystalline Rebaudioside A powder;

B) providing a solvent consisting essentially of water at a 1:1 ratio with the crystalline Rebaudioside A powder;

C) mixing the solvent and crystalline Rebaudioside A powder to make a mixture;

D) increasing the temperature of the mixture by a gradient heat treatment method having a rate of temperature change of about 1° C. per minute to an elevated temperature of about 100-140° C. to make a solution;

E) holding the solution al the elevated temperature; and

F) decreasing the temperature of the solution by a gradient cooling method having a regular rate of temperature change, wherein the solution contains the crystalline Rebaudioside A and has a clear solution stability without visible crystallization or cloudiness at 25° C. for up to 24 hours at 50% total solids content.

* * * * *